United States Patent
Shiramizu

(10) Patent No.: US 6,248,997 B1
(45) Date of Patent: Jun. 19, 2001

(54) METHOD OF ANALYZING SUBSTANCES EXISTING IN GAS

(75) Inventor: Yoshimi Shiramizu, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/243,853

(22) Filed: Feb. 3, 1999

(30) Foreign Application Priority Data

Feb. 4, 1998 (JP) .................................... 10-023146

(51) Int. Cl.[7] ........................................ H01J 49/04
(52) U.S. Cl. ............................. 250/282; 250/288
(58) Field of Search .................... 250/288, 282

(56) References Cited

U.S. PATENT DOCUMENTS 5,272,337 * 12/1993 Thompson et al. ............... 250/288
5,528,032 * 6/1996 Uchiyama ......................... 250/288

FOREIGN PATENT DOCUMENTS

| 1 435 284 | 5/1976 | (GB) . |
| 2 250 633 | 6/1992 | (GB) . |
| 2 288 234 | 10/1995 | (GB) . |
| 2 320 569 | 6/1998 | (GB) . |

* cited by examiner

Primary Examiner—Jack Berman

(57) ABSTRACT

A method of analyzing substances is provided, which improves the correctness in analysis of desired substances applying some bad effect to a semiconductor device. In the first step, a gas to be analyzed is contacted with an absorbent, thereby absorbing substances existing in the gas to the absorbent. The absorbent is made of a same material as that of a semiconductor material to be processed in the gas. In the second step, the absorbent is heated to thermally desorb the absorbed substances from the absorbent at a specific thermally desorbing temperature. In the third step, the desorbed substances are physically separated to be identified by using an analytical system. Preferably, the absorbent used in the first step is made of bits or particles of polycrystalline, single-crystal, or amorphous Si. The absorbent is preferably located in a hollow refractory tube and the gas is injected into the tube in the first step.

15 Claims, 1 Drawing Sheet

METHOD OF ANALYZING SUBSTANCES EXISTING IN GAS

BACKGROUND OF THE INVENTION

1. Field of the Invention

The present invention relates to an analytical method of substances and more particularly, to a method of analyzing substances existing in a gas (e.g., air) to find and identify contaminants existing therein, which is preferably used for evaluating the environment or atmosphere in a cleanroom that has been popularly used in fabrication of semiconductor devices.

2. Description of the Prior Art

Usually, the air existing in a cleanroom used for fabrication of semiconductor devices contains various organic substances that apply bad effects to the devices. For example, if some organic substances (i.e., organic contaminants) are adhered onto a single-crystal silicon (Si) wafer, the adhered substances or contaminants may lower the dielectric strength of silicon dioxide ($SiO_2$) films provided for the electronic elements (e.g., transistors) formed on or over the Si wafer. Alternately, the adhered substances or contaminants may weaken the cleaning effects of cleaning chemicals used in photolithography and etching processes or the like, resulting in insufficient removal of native oxides and/or metallic impurities.

Conventionally, the organic substances existing in the air in the cleanroom, which serve as contaminants for the popular Si devices, have been measured or identified in the following way.

First, a resin-based absorbent is packed into an absorption tube and then, the air existing in the cleanroom is injected into the tube as a sample by using a proper pumping system. Thus, organic substances contained in the injected sample air are absorbed or trapped by the absorbent. Thereafter, the absorption tube is heated to thermally desorb the absorbed substances from the absorbent at a high temperature of approximately 250° C. to 300° C.

Subsequently, the thermally-desorbed organic substances are analyzed by the use of a gas chromatograph and a mass spectrometer. Specifically, the thermally-desorbed substances in the absorption tube are first sent to the gas chromatograph by a carrier gas and physically separated therein. Next, the substances thus physically separated are sent to the mass spectrometer and analyzed qualitatively and quantitatively therein. As a result, the organic substances existing in the sample air are identified.

With the above-described conventional method, a lot of undesired organic substances that apply no bad effect to the semiconductor devices are detected. This is because the resin-based absorbent used in the conventional method is made of an organic material having a property to absorb almost all the existing organic substances. Therefore, the desorbed organic substances from the absorbent are likely to contain the undesired organic substances.

The undesired organic substances serve as a noise source in the analysis for detecting the desired organic substances that apply some bad effect to the semiconductor devices. In other words, the undesired organic substances cause insufficient physical separation of the organic substances to be analyzed in the gas chromatograph, resulting in incorrect qualitative and quantitative analysis in the mass spectrometer.

Consequently, there arises a problem that the desired organic substances are unable to be analyzed with satisfactory correctness.

Moreover, to thermally desorb the absorbed organic substances from the absorbent efficiently, it is preferred that the thermally desorbing temperature is as high as possible. However, because the resin-based absorbent used in the conventional method is usually made of an organic material, the thermally desorbing temperature needs to be set at a comparatively low temperature of approximately 250 to 300° C.

Thus, there arises another problem that the thermally desorbing temperature is unable to be raised as desired.

SUMMARY OF THE INVENTION

Accordingly, an object of the present invention to provide a method of analyzing substances that improves the correctness in analysis of desired substances applying some bad effect to a semiconductor device.

Another object of the present invention to provide a method of analyzing substances that makes it possible to selectively analyze the desired substances.

Still another object of the present invention to provide a method of analyzing substances that decreases the noise occurring in analysis.

A further object of the present invention to provide a method of analyzing substances that raises the thermally desorbing temperature of the absorbed substances.

The above objects together with others not specifically mentioned will become clear to those skilled in the art from the following description.

A method of analyzing substances existing in a gas according to the present invention is comprised of the following first to third steps.

In the first step, a gas to be analyzed is contacted with an absorbent, thereby absorbing substances existing in the gas to the absorbent. The absorbent is made of a same material as that of a semiconductor material to be processed in the gas.

In the second step, the absorbent is heated to thermally desorb the absorbed substances from the absorbent at a specific thermally desorbing temperature.

In the third step, the desorbed substances are separated and identified by using an analytical system.

With the method of analyzing substances according to the present invention, in the first step, the gas to be analyzed is contacted with the absorbent, thereby absorbing the substances existing in the gas to the absorbent. The absorbent is made of a same material as that of the semiconductor material to be processed in the gas.

Therefore, each of the substances absorbed to the absorbent has a property of being absorbed to the semiconductor material to be processed in the gas. In other words, any substance having a property of not being absorbed to the semiconductor material is not absorbed to the absorbent.

As a result, the desorbed substances from the absorbent do not contain undesired substances applying no bad effect to a semiconductor device formed by the use of the semiconductor material. This means that the undesired substances are not analyzed by the analytical system in the third step, and that the noise due to the undesired substances is decreased or eliminated.

Thus, the desired substances applying some bad effect to the semiconductor device are selectively analyzed in the third step, which improves the correctness in analysis of the desired substances.

Moreover, the absorbent used in the first step is made of a same material as that of the semiconductor material to be processed in the gas. Therefore, the thermally desorbing temperature in the second step can be raised compared with the conventional method using the resin-based absorbent.

In a preferred embodiment of the method according to the present invention, the absorbent used in the first step is made of bits or particles of Si. Si may be polycrystalline, single-crystalline, or amorphous. In this embodiment, the advantages of the present invention are remarkably exhibited, because Si is a very popular material in the fabrication processes of the semiconductor device.

It is more preferred that the absorbent is made of bits or particles of polycrystalline Si (i.e., polysilicon) because this is readily accessible in the fabrication processes of the semiconductor device.

In another preferred embodiment of the method according to the present invention, in the first step, the absorbent is located in a hollow refractory tube and the gas is injected into the tube. In this embodiment, it is more preferred that the tube is made of quartz, because quartz has a high heat-resistant property and is readily accessible.

In still another preferred embodiment of the method according to the present invention, the third step is carried out by using a gas chromatograph. In this embodiment, it is more preferred that a mass analyzer is used as a detector for the gas chromatograph in the third step.

In a further preferred embodiment of the method according to the present invention, the gas to be analyzed is the air existing in a cleanroom used for fabrication of semiconductor devices. In this embodiment, the advantages of the present invention are remarkably exhibited. It is more preferred that the substances are organic, because organic substances tend to apply bad effects to the semiconductor device.

BRIEF DESCRIPTION OF THE DRAWINGS

In order that the present invention may be readily carried into effect, it will now be described with reference to the accompanying drawings.

DETAILED DESCRIPTION OF THE PREFERRED EMBODIMENTS

Figure 1:
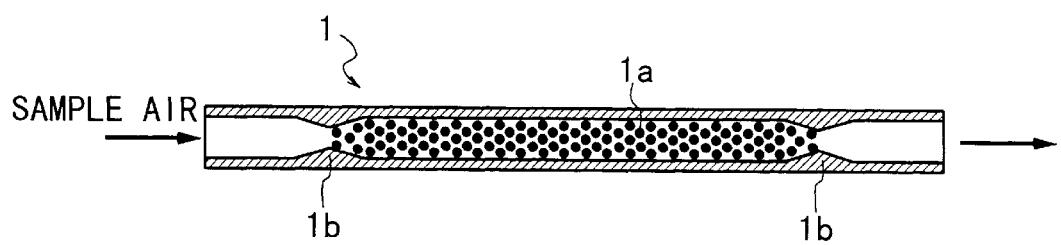
FIG. 1 is a schematic cross-sectional view of the absorption tube, which shows the process of absorbing the organic substances existing in the sample air onto the absorbent packed in the absorption tube in a method of analyzing substances according to an embodiment of the present invention.

Preferred embodiments of the present invention will be described in detail below while referring to the drawings attached.

In a method of analyzing substances according to an embodiment of the present invention, the air existing in a cleanroom which is used for fabrication of Si devices is used as a sample. In other words, the cleanroom air is used as a sample to be analyzed in this method. Therefore, the cleanroom air serving as the sample may be termed the "sample air".

To trap organic substances contained in the sample air, a hollow absorption tube 1 shown in FIG. 1 is used. This tube 1, which has a cylindrical shape with two opening ends, includes polysilicon particles 1a as an absorbent. Here, the particles 1a have a diameter of approximately 1 $\mu$m. However, the particles 1a may have any other diameter than approximately 1 $\mu$m if they provide satisfactorily wide surface areas (i.e., absorption areas).

Two protrusions 1b are formed in the inner hollow path of the tube 1 near its two ends. The polysilicon particles 1a are fixed in the middle part of the tube 1 partitioned by the protrusions 1b.

The sample air is introduced into the absorption tube 1 from its one opening end by the use of a vacuum pump (not shown) or the like and then, the sample air thus introduced is emitted from the other opening end thereof. During this process, the organic substances contained in the sample air are absorbed onto the polysilicon particles 1a serving as the absorbent. Thus, the organic substances in the sample air are trapped.

Here, the organic substances thus absorbed onto the polysilicon particles 1a, which have been contained in the sample air, are termed the "sample organic substances" or "sample substances".

Subsequently, the absorption tube 1 containing the sample organic substances is subjected to gas chromatography as explained below.

Figure 2:
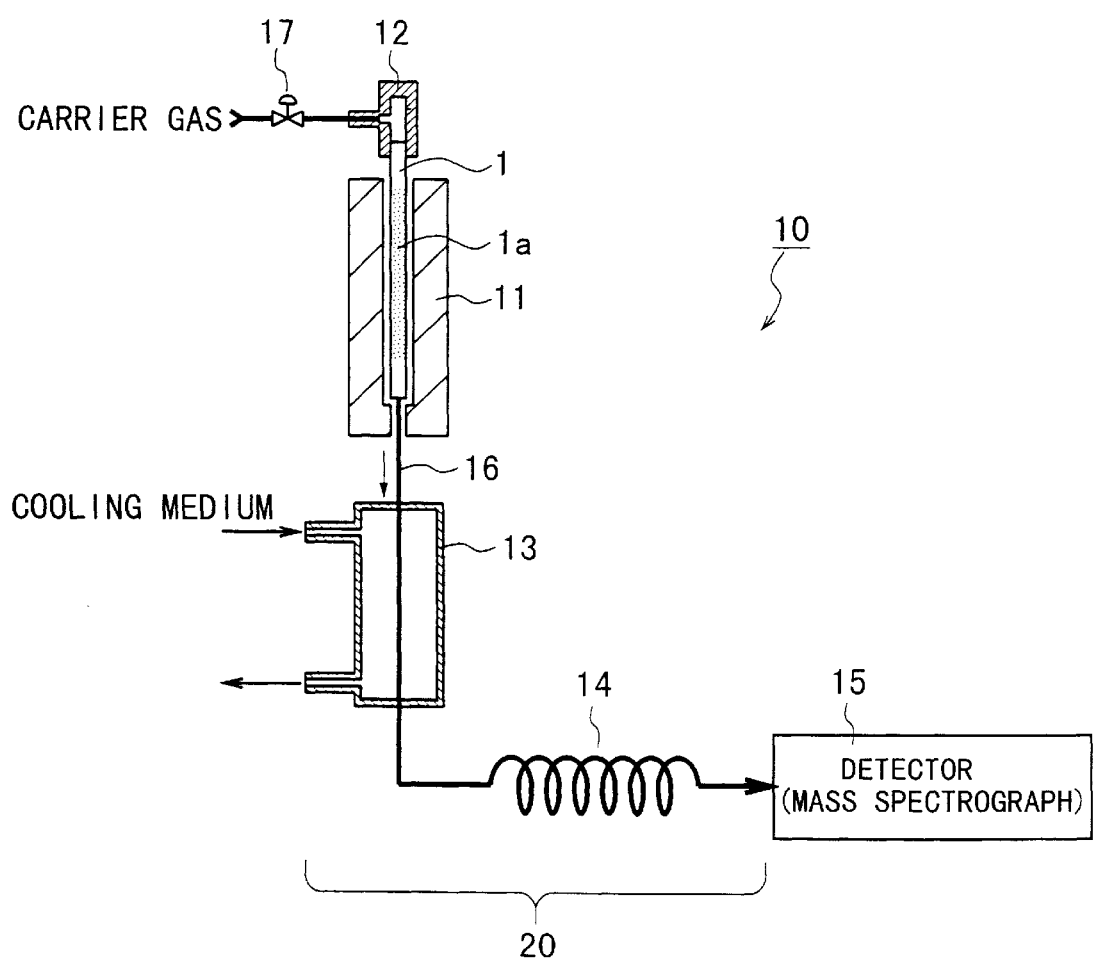
FIG. 2 is a schematic view showing the configuration of an analytical system used for the method of analyzing substances according to the embodiment of the present invention.

An analytical instrument or system used for performing the method according to the embodiment of the present invention is schematically shown in FIG. 2, in which the analytical system is referred as 10.

As seen from FIG. 2, the analytical system 10 is comprised of a heater 11, a carrier-gas supplier 12, a cryo-focusing subsystem 13, a separation column 14, and a detector 15.

The heater 11 has a tube-receiving hole into which one of the opening ends of the absorption tube 1 is inserted. The heater 11 serves to heat the absorption tube 1 that has been inserted to the hole of the heater 11, thereby desorbing the sample organic substances absorbed onto the polysilicon particles 1a therefrom.

The carrier-gas supplier 12 has a port to which one of the opening ends of the absorption tube 1 is inserted and connected. After the specific end of the tube 1 is connected to the port, the supplier 12 starts to supply a specific carrier gas such as helium (He) to the tube 1 while controlling the flow rate of the carrier gas by a mass flow controller 17. The carrier gas serves to carry or transmit the sample organic substances that have been thermally desorbed from the polysilicon particles 1a in the absorption tube 1. The other end of the tube 1 is connected to the separation column 14 through a connection pipe 16.

The cryo-focusing subsystem 13 is located to cover a specific part of the connection pipe 16 between the heater 11 and the column 14. The subsystem 13 is supplied with a cooling medium such as liquid nitrogen (N) to thereby cool down the carrier gas and the desorbed sample substances that move along the pipe 16. The cooling medium thus supplied is then returned to its source (not shown) for circulation. Due to the cooling down by the subsystem 13, the carrier gas transmitting the desorbed sample substances is reduced in volume or concentrated.

The separation column 14 serves to separate physically the sample organic substances transmitted by the carrier gas by the use of a known principle. The sample substances thus separated are sent to a mass spectrograph serving as the detector 15.

The heater 11, the carrier-gas supplier 12, the cryo-focusing subsystem 13, and the separation column 14 constitute a gas chromatograph 20.

The detector 15 serves to analyze the separated sample organic substances qualitatively and quantitatively, thereby identifying the organic substances or contaminants existing in the sample air (i.e., the air existing in the cleanroom).

Next, the method of analyzing substances according to the embodiment of the present invention is explained in detail below.

First, the absorption tube 1 in which the polysilicon particles 1a with a diameter of approximately 1 $\mu$m are packed as an absorbent is prepared. Then, the air existing in the cleanroom is introduced into the tube 1 as the sample (i.e., the sample air) by the use of a pump to be contacted with the particles 1a. Thus, the organic substances contained in the sample air, each of which has a property of being physically absorbed to polysilicon, are selectively absorbed onto the polysilicon particles 1a.

Next, the absorption tube 1 is inserted into the tube-receiving hole of the heater 11 and then, the port of the carrier-gas supplier 12 is connected to the one end of the tube 1. At the same time, the opposing end of the connection pipe 16 is connected to the other end of the tube 1, where the other end of the pipe 16 communicates with the column 14.

Thereafter, while supplying the specific carrier gas to the inside of the absorption tube 1, the tube 1 is heated by the heater 11 to a specific thermally desorbing temperature, thereby desorbing the organic substances absorbed onto the polysilicon particles 1a (i.e., the sample organic substances) therefrom. Thus, the desorbed sample substances are carried to the connection pipe 16 by the flow of the carrier gas.

The heating or thermally-desorbing temperature may be approximately 250 to 300° C. which is the same as that used in the previously-explained conventional method. However, it is preferred that the heating temperature is set at a value higher than 300° C., this is because the sample substances are desorbed from the polysilicon particles 1a more efficiently. In this case, the highest heating temperature, which is determined dependent on the thermal decomposition temperatures of the sample organic substances, is typically set as 400 to 450° C.

Even if the heating temperature is raised to the thermal decomposition temperatures of the sample substances, there is a possibility that some of the sample organic substances may be left on the polysilicon particles 1a. In this case, the heating temperature needs to be raised to 500° C. or higher; however, the highest heating temperature needs to be lower than the melting point of the polysilicon particles 1a. To cope with this need, it is necessary to produce the absorption tube 1 by a refractory material such as quartz.

Following the heating or thermally desorbing process, the sample organic substances thus desorbed are moved by the carrier gas to the column 14 through the cryo-focusing subsystem 13. The carrier gas containing the sample substances is cooled by the cryo-focusing subsystem 13 and decreased in volume. In other words, the carrier gas containing the sample substances is concentrated.

The concentrated carrier gas containing the sample organic substances is then subjected to physical separation in the column 14. Thus, the sample organic substances are physically separated from one another based on a known separation principle of gas chromatograph.

Finally, the individual sample substances thus separated are sent to the mass spectrograph serving as the detector 15 along with the carrier gas and then, they are simultaneously analyzed qualitatively and quantitatively. As a result, the organic substances or contaminants contained in the sample air (i.e. the air existing in the cleanroom) are found and identified.

With the method of analyzing substances according to the embodiment of the present invention, as described above, the polysilicon particles 1a are used as the absorbent for trapping the sample organic substances contained in the cleanroom air. Therefore, the absorbed organic substances are likely to be absorbed onto a single-crystal Si wafer that has been popularly used for Si device fabrication. Also, the volatile organic substances that are difficult to be absorbed onto the Si wafer are not absorbed onto the polysilicon particles 1a even it they exist in the cleanroom air.

Accordingly, only the organic substances that will be absorbed onto the Si wafer, i.e., the desired organic substances that apply some bad effect to the Si devices, can be selectively analyzed. In other words, any substance having a property of not being absorbed onto the Si wafer is not analyzed, which means that the noise due to the undesired substances is decreased or eliminated.

Moreover, since the absorbent is made of polysilicon which is a same material as that of the Si material to be processed in the cleanroom air, the heating temperature in the thermally desorbing process can be raised compared with the previously-explained conventional method using the resin-based absorbent.

To confirm the advantages of the present invention, the inventor performed a confirmation test. In this test, the method of the present invention was actually carried out according to the above-explained embodiment using polysilicon particles as an absorbent. The previously-explained conventional method was actually carried out using a resin-based absorbent termed "TENAX TA", which was produced by a company termed TENAX FIBERS GmbH & Co.KG.

The result of this test is shown in Tables 1 and 2 shown below.

TABLE 1

| DETECTED SUBSTANCE | | QUANTITY ($\mu g/m^3$) |
|---|---|---|
| No. 1 | $C_4H_{12}O_2$ | 11 |
| No. 2 | toluene | 9.1 |
| No. 3 | $C_6H_{12}O_2$ | 2.8 |
| No. 4 | xylene | 4.3 |
| No. 5 | MEK | 15 |
| No. 6 | $C_6H_{12}O_2$ | 6.8 |
| No. 7 | anti-oxidizing agents | 19 |
| No. 8 | phthalic-acid-based chemicals | — |
| No. 9 | hydrocarbon | 7.0 |

In the conventional method, as seen from Table 1, eight organic substances (Nos. 1–7, and No. 9) were detected and identified. In Table 1, the word "MEK" means "methyl ethyl ketone".

TABLE 2

| DETECTED SUBSTANCE | | QUANTITY ($\mu g/m^3$) |
|---|---|---|
| No. 1 | MEK | 15 |
| No. 2 | $C_5H_{11}HO$ | — |
| No. 3 | $C_8H_{18}O$ | 4.3 |
| No. 4 | $C_7H_5NS$ | 0.6 |
| No. 5 | $C_7H_{11}NS$ | 1.5 |
| No. 6 | $C_3Cl_3F_3$ | 0.9 |
| No. 7 | DBP (phthalic-acid-based chemicals) | — |
| No. 8 | $C_{16}H_{32}O_2$ | 1.4 |
| No. 9 | hydrocarbon | 67 |

On the other hand, in the method of the present invention, as seen from Table 2, seven organic substances (No. 1, Nos. 3–6, and Nos. 8 and 9) were detected and identified. In Table 2, "DBP" means "dibuthyl phthalate".

As clearly seen from Tables 1 and 2, the organic substances with the Nos. 1 to 4 and Nos. 6 and 7 detected in the conventional method (Table 1) were not detected in the method according to the invention (Table 2). This is because these substances are likely to volatile even if they are absorbed onto the Si wafer, or they are difficult to be absorbed onto the Si wafer. Therefore, these substances do not form a cause of raising any problem in the Si devices.

Contrarily, as seen from Table 2, the substances that will be actually absorbed onto the Si wafer were selectively detected in the method according to the invention. Therefore, it is seen that the substances that will form a cause of raising some problem in the Si devices are able to be detected selectively in the this method.

In the conventional method also, as seen from Table 1, the substances that will form a cause of raising some problem in the Si devices (e.g., the substance Nos. 8 and 9 in Table 1) were detected. However, various organic substances that form a cause of raising any problem in the Si devices were detected, which form the noise that impedes the correct analysis for the desired organic substances. Unlike this, in the method according to the invention, the desired organic substances affecting badly to the Si devices can be selectively detected while decreasing the noise.

Although polysilicon particles 1a are used as the absorbent in the above embodiment of the present invention, it is needless to say that single-crystal Si or amorphous Si may be used as the absorbent.

Additionally, the mark "- - -" in Tables 1 and 2 means the fact that the corresponding substance was not detected, i.e., the detected quantity was less than the detection limit of the mass spectrograph.

In the above-described embodiment, the present invention is applied to analysis of the organic substances that will be absorbed onto a single-crystal Si wafer. However, it is needless to say that the present invention may be applied to analysis of any other semiconductor material than Si (e.g., compound semiconductor materials such as GaAs) if it is the same as the desired material to be analyzed.

While the preferred form of the present invention has been described, it is to be understood that modifications will be apparent to those skilled in the art without departing from the spirit of the invention. The scope of the invention, therefore, is to be determined solely by the following claims.

What is claimed is:

1. A method of analyzing substances existing in a gas, comprising:
    (a) a first step of contacting a gas to be analyzed with an absorbent, thereby absorbing substances existing in said gas to said absorbent;
        said absorbent being made of bits or particles of a same material as that of a semiconductor material to be processed in said gas;
    (b) a second step of heating said absorbent to thermally desorb said absorbed substances from said absorbent at a specific thermally desorbing temperature; and
    (c) a third step of separating and identifying said desorbed substances by using an analytical system.

2. The method as claimed in claim 1, wherein said absorbent used in said first step is made of bits or particles of silicon.

3. The method as claimed in claim 1, wherein said absorbent used in said first step is made of bits or particles of polysilicon.

4. The method as claimed in claim 1, wherein said absorbent is located in a hollow refractory tube and said gas is injected into said tube in said first step.

5. The method as claimed in claim 1, wherein said third step is carried out by using a gas chromatograph.

6. The method as claimed in claim 5, wherein a mass spectrograph is used along with said gas chromatograph in said third step.

7. The method as claimed in claim 1, wherein said gas to be analyzed is the air existing in a cleanroom used for fabrication of semiconductor devices.

8. The method as claimed in claim 1, wherein said substances are organic.

9. A method of analyzing substances existing in a gas, comprising:
    (a) a first step of contacting a gas to be analyzed with an absorbent, thereby absorbing substances existing in said gas to said absorbent;
        said absorbent being made of a same material as that of a semiconductor material to be processed in said gas;
    (b) a second step of heating said absorbent to thermally desorb said absorbed substances from said absorbent at a specific thermally desorbing temperature; and
    (c) a third step of separating and identifying said desorbed substances by using an analytical system,
        wherein said absorbent is located in a hollow refractory tube and said gas is injected into said tube in said first step.

10. The method as claimed in claim 9, wherein said absorbent used in said first step is made of bits or particles of silicon.

11. The method as claimed in claim 9, wherein said absorbent used in said first step is made of bits or particles of polysilicon.

12. The method as claimed in claim 9, wherein said third step is carried out by using a gas chromatograph.

13. The method as claimed in claim 12, wherein a mass spectrograph is used along with said gas chromatograph in said third step.

14. The method as claimed in claim 9, wherein said gas to be analyzed is the air existing in a cleanroom used for fabrication of semiconductor devices.

15. The method as claimed in claim 9, wherein said substances are organic.

* * * * *

UNITED STATES PATENT AND TRADEMARK OFFICE
CERTIFICATE OF CORRECTION

PATENT NO.    : 6,248,997 B1
DATED         : June 19, 2001
INVENTOR(S)   : Yoshimi Shiramizu It is certified that error appears in the above-identified patent and that said Letters Patent is hereby corrected as shown below:

Title page,
Item [56], the following is added under the title patent documents in the References Cited,

| | | |
|---|---|---|
| -- 60-243538 | 12/1985 | (JP) |
| 7-83808 | 3/1995 | (JP) |
| 7-174746 | 7/1995 | (JP) |
| 9-43117 | 2/1997 | (JP) |
| 9-43211 | 2/1997 | (JP) |

Signed and Sealed this

Ninth Day of April, 2002

Attest:

Attesting Officer

JAMES E. ROGAN
*Director of the United States Patent and Trademark Office*